United States Patent
Kim et al.

(10) Patent No.: US 9,580,490 B2
(45) Date of Patent: Feb. 28, 2017

(54) USES OF MODIFIED HUMAN TUMOR NECROSIS FACTOR RECEPTOR-1 POLYPEPTIDE

(71) Applicant: Hanall Biopharma Co., Ltd., Daegu (KR)

(72) Inventors: Sung Wuk Kim, Gyeonggi-do (KR); Seung Kook Park, Seoul (KR); Yeon Jung Song, Gyeonggi-do (KR); Eun Sun Kim, Seoul (KR); Hyea Kyung Ahn, Gyeonggi-do (KR); Jae Kap Jeong, Gyeonggi-do (KR); Hung Keun Lee, Seoul (KR)

(73) Assignee: HANALL BIOPHARMA CO., LTD., Daegu (KR)

( * ) Notice: Subject to any disclaimer, the term of this patent is extended or adjusted under 35 U.S.C. 154(b) by 0 days.

(21) Appl. No.: 14/404,001

(22) PCT Filed: Feb. 7, 2013

(86) PCT No.: PCT/KR2013/000983
§ 371 (c)(1),
(2) Date: Nov. 25, 2014

(87) PCT Pub. No.: WO2013/191352
PCT Pub. Date: Dec. 27, 2013

(65) Prior Publication Data
US 2015/0119338 A1    Apr. 30, 2015

(30) Foreign Application Priority Data
Jun. 21, 2012 (KR) .................. 10-2012-0066527

(51) Int. Cl.
*A61K 38/00* (2006.01)
*A61K 38/17* (2006.01)
*C07K 14/715* (2006.01)
*C07K 14/705* (2006.01)

(52) U.S. Cl.
CPC ....... *C07K 14/7151* (2013.01); *A61K 38/1793* (2013.01); *C07K 14/70575* (2013.01)

(58) Field of Classification Search
None
See application file for complete search history.

(56) References Cited

U.S. PATENT DOCUMENTS

| 6,177,077 | B1 | 1/2001 | Tobinick |
| 6,204,270 | B1 | 3/2001 | Ron et al. |
| 6,379,666 | B1 | 4/2002 | Tobinick |
| 6,428,787 | B1 | 8/2002 | Tobinick |
| 9,068,019 | B2 | 6/2015 | Kim et al. |
| 2004/0126372 | A1 | 7/2004 | Banerjee et al. |
| 2009/0098136 | A1 | 4/2009 | Gamache et al. |
| 2011/0117082 | A1 | 5/2011 | Liu et al. |
| 2012/0277142 | A1 | 11/2012 | Kim et al. |
| 2013/0237472 | A1 | 9/2013 | Kim et al. |

FOREIGN PATENT DOCUMENTS

| KR | 10-2012-0027666 A | 3/2012 |
| WO | 0027421 A2 | 5/2000 |
| WO | 2012036410 A2 | 3/2012 |

OTHER PUBLICATIONS

Schaumburg, C., et al., "Ocular Surface APCs Are Necessary for Autoreactive T Cell-Mediated Experimental Autoimmune Lacrimal Keratoconjunctivitis", "The Journal of Immunology", Aug. 31, 2011, pp. 3653-3662, vol. 187.

*Primary Examiner* — Michael Pak
(74) *Attorney, Agent, or Firm* — Hultquist, PLLC; Steven J. Hultquist

(57) ABSTRACT

The present invention relates to new uses of modified human tumor necrosis factor receptor-1 (TNFRI) polypeptide, and more particularly, to uses thereof for prevention and treatment of dry eye syndrome. The modified TNFRI or modified TNFRI fragment of the present invention has excellent TNFα neutralizing activity, and inhibits TNFα activity on the ocular surface of the patient to suppress inflammation induction effects related to dry eye. Therefore, the modified TNFRI or modified TNFRI fragment of the present invention exhibits remarkable effects in the prevention and treatment of dry eye syndrome, and thus can be very useful in the prevention and treatment of dry eye syndrome.

13 Claims, 3 Drawing Sheets

SEQUENCE LISTING

```
<160> NUMBER OF SEQ ID NOS: 30

<210> SEQ ID NO 1
<211> LENGTH: 455
<212> TYPE: PRT
<213> ORGANISM: Homo sapiens

<400> SEQUENCE: 1

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
        50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205
```

Gly Thr Thr Val Leu Leu Pro Leu Val Ile Phe Phe Gly Leu Cys Leu
210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
        450                 455

<210> SEQ ID NO 2
<211> LENGTH: 171
<212> TYPE: PRT
<213> ORGANISM: Homo sapiens

<400> SEQUENCE: 2

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Ser Glu Asn His Leu Arg His Cys Leu Ser Cys Ser Lys
        50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

```
His Ala Gly Phe Phe Leu Arg Glu Asn Glu Cys Val Ser Cys Ser Asn
        130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170

<210> SEQ ID NO 3
<211> LENGTH: 126
<212> TYPE: PRT
<213> ORGANISM: Homo sapiens

<400> SEQUENCE: 3

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125

<210> SEQ ID NO 4
<211> LENGTH: 105
<212> TYPE: PRT
<213> ORGANISM: Homo sapiens

<400> SEQUENCE: 4

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
            100                 105

<210> SEQ ID NO 5
<211> LENGTH: 455
<212> TYPE: PRT
<213> ORGANISM: Artificial
<220> FEATURE:
<223> OTHER INFORMATION: TNFRI-A2 S92I/H95F/R97P

```
<400> SEQUENCE: 5

Met Gly Leu Ser Thr Val Pro Asp Leu Leu Pro Leu Val Leu Leu
1               5                   10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
50                      55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ile Glu Asn Phe Leu
                85                  90                  95

Pro Ala Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
            115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
            195                 200                 205

Gly Thr Thr Val Leu Leu Pro Leu Val Ile Phe Phe Gly Leu Cys Leu
210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
            275                 280                 285

Pro Ser Ser Thr Phe Thr Ser Ser Ser Thr Tyr Thr Pro Gly Asp Cys
            290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
            355                 360                 365

Leu Arg Trp Lys Glu Phe Val Arg Arg Leu Gly Leu Ser Asp His Glu
370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415
```

```
Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
            435                 440                 445

Pro Ala Pro Ser Leu Leu Arg
            450                 455

<210> SEQ ID NO 6
<211> LENGTH: 455
<212> TYPE: PRT
<213> ORGANISM: Artificial
<220> FEATURE:
<223> OTHER INFORMATION: TNFRI-A9 S92M/H95F/R97P/H98A

<400> SEQUENCE: 6

Met Gly Leu Ser Thr Val Pro Asp Leu Leu Pro Leu Val Leu Leu
1

```
Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455

<210> SEQ ID NO 7
<211> LENGTH: 455
<212> TYPE: PRT
<213> ORGANISM: Artificial
<220> FEATURE:
<223> OTHER INFORMATION: TNFRI-S36 L68V/S92M/H95F/R97P/H98A

<400> SEQUENCE: 7

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Val Tyr Asn Asp Cys Pro Gly Pro Gly Gln Asp Thr Asp
65                  70                  75                  80

Cys Arg Glu Cys Glu Ser Gly Ser Phe Thr Ala Met Glu Asn Phe Leu
                85                  90                  95

Pro Ala Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220
```

```
Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
            245                 250                 255

Gly Glu Leu Glu Gly Thr Thr Thr Lys Pro Leu Ala Pro Asn Pro Ser
        260                 265                 270

Phe Ser Pro Thr Pro Gly Phe Thr Pro Thr Leu Gly Phe Ser Pro Val
    275                 280                 285

Pro Ser Ser Thr Phe Thr Ser Ser Thr Tyr Thr Pro Gly Asp Cys
290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
            325                 330                 335

Pro Leu Gln Lys Trp Glu Asp Ser Ala His Lys Pro Gln Ser Leu Asp
        340                 345                 350

Thr Asp Asp Pro Ala Thr Leu Tyr Ala Val Val Glu Asn Val Pro Pro
    355                 360                 365

Leu Arg Trp Lys Glu Phe Val Arg Arg Leu Gly Leu Ser Asp His Glu
370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
            405                 410                 415

Thr Leu Glu Leu Leu Gly Arg Val Leu Arg Asp Met Asp Leu Leu Gly
        420                 425                 430

Cys Leu Glu Asp Ile Glu Glu Ala Leu Cys Gly Pro Ala Ala Leu Pro
    435                 440                 445

Pro Ala Pro Ser Leu Leu Arg
450                 455

<210> SEQ ID NO 8
<211> LENGTH: 455
<212> TYPE: PRT
<213> ORGANISM: Artificial
<220> FEATURE:
<223> OTHER INFORMATION: TNFRI-S54 L68V/S92I/H95F/R97P/H98A/K161N

<400> SEQUENCE: 8

Met Gly Leu Ser Thr Val Pro Asp Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Val Tyr Asn Asp Cys Pro Gly Pro Gly Gln Asp Thr Asp
65                  70                  75                  80

Cys Arg Glu Cys Glu Ser Gly Ser Phe Thr Ala Ile Glu Asn Phe Leu
            85                  90                  95

Pro Ala Cys Leu Ser Cys Ser Lys Cys Arg Lys Glu Met Gly Gln Val
        100                 105                 110

Glu Ile Ser Ser Cys Thr Val Asp Arg Asp Thr Val Cys Gly Cys Arg
    115                 120                 125
```

Lys Asn Gln Tyr Arg His Tyr Trp Ser Glu Asn Leu Phe Gln Cys Phe
            130                 135                 140

Asn Cys Ser Leu Cys Leu Asn Gly Thr Val His Leu Ser Cys Gln Glu
145                 150                 155                 160

Asn Gln Asn Thr Val Cys Thr Cys His Ala Gly Phe Phe Leu Arg Glu
            165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
            195                 200                 205

Gly Thr Thr Val Leu Leu Pro Leu Val Ile Phe Phe Gly Leu Cys Leu
            210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
            245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
            275                 280                 285

Pro Ser Ser Thr Phe Thr Ser Ser Ser Thr Tyr Thr Pro Gly Asp Cys
290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
            325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
            355                 360                 365

Leu Arg Trp Lys Glu Phe Val Arg Arg Leu Gly Leu Ser Asp His Glu
            370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
            405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
            435                 440                 445

Pro Ala Pro Ser Leu Leu Arg
    450                 455

<210> SEQ ID NO 9
<211> LENGTH: 455
<212> TYPE: PRT
<213> ORGANISM: Artificial
<220> FEATURE:
<223> OTHER INFORMATION: TNFRI-S57 L68V/S92M/H95F/R97P/H98A/K161N

<400> SEQUENCE: 9

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro

```
His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Val Tyr Asn Asp Cys Pro Gly Pro Gly Gln Asp Thr Asp
65                  70                  75                  80

Cys Arg Glu Cys Glu Ser Gly Ser Phe Thr Ala Met Glu Asn Phe Leu
                85                  90                  95

Pro Ala Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Asn Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445
```

Pro Ala Pro Ser Leu Leu Arg
    450                 455

<210> SEQ ID NO 10
<211> LENGTH: 455
<212> TYPE: PRT
<213> ORGANISM: Artificial
<220> FEATURE:
<223> OTHER INFORMATION: TNFRI-S58 L68V/S92M/H95F/R97P/H98A/D207N

<400> SEQUENCE: 10

Met Gly Leu Ser Thr Val Pro Asp Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                      60

Gly Thr Tyr Val Tyr Asn Asp Cys Pro Gly Pro Gly Gln Asp Thr Asp
65                  70                  75                  80

Cys Arg Glu Cys Glu Ser Gly Ser Phe Thr Ala Met Glu Asn Phe Leu
                85                  90                  95

Pro Ala Cys Leu Ser Cys Ser Lys Cys Arg Lys Glu Met Gly Gln Val
                100                 105                 110

Glu Ile Ser Ser Cys Thr Val Asp Arg Asp Thr Val Cys Gly Cys Arg
            115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asn Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
                420                 425                 430

Cys Leu Glu Asp Ile Glu Glu Ala Leu Cys Gly Pro Ala Ala Leu Pro
            435                 440                 445

Pro Ala Pro Ser Leu Leu Arg
    450                 455

<210> SEQ ID NO 11
<211> LENGTH: 455
<212> TYPE: PRT
<213> ORGANISM: Artificial
<220> FEATURE:
<223> OTHER INFORMATION: TNFRI-S62 L68V/S92I/H95F/R97P/H98G/K161Q

<400> SEQUENCE: 11

Met Gly Leu Ser Thr Val Pro Asp Leu Leu Pro Leu Val Leu Leu
1               5                   10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
        50                  55                  60

Gly Thr Tyr Val Tyr Asn Asp Cys Pro Gly Pro Gly Gln Asp Thr Asp
65                  70                  75                  80

Cys Arg Glu Cys Glu Ser Gly Ser Phe Thr Ala Ile Glu Asn Phe Leu
                85                  90                  95

Pro Gly Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

-continued

```
Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
    275                 280                 285

Pro Ser Ser Thr Phe Thr Ser Ser Ser Thr Tyr Thr Pro Gly Asp Cys
290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
            355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
            435                 440                 445

Pro Ala Pro Ser Leu Leu Arg
450                 455

<210> SEQ ID NO 12
<211> LENGTH: 455
<212> TYPE: PRT
<213> ORGANISM: Artificial
<220> FEATURE:
<223> OTHER INFORMATION: TNFRI-S63 L68V/S92M/H95F/R97P/H98G/K161N

<400> SEQUENCE: 12

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Val Tyr Asn Asp Cys Pro Gly Pro Gly Gln Asp Thr Asp
65                  70                  75                  80

Cys Arg Glu Cys Glu Ser Gly Ser Phe Thr Ala Met Glu Asn Phe Leu
                85                  90                  95

Pro Gly Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160
```

```
Asn Gln Asn Thr Val Cys Thr Cys His Ala Gly Phe Phe Leu Arg Glu
                165                 170                 175
Asn Glu Cys Val Ser Cys Ser Asn Cys Lys Lys Ser Leu Glu Cys Thr
            180                 185                 190
Lys Leu Cys Leu Pro Gln Ile Glu Asn Val Lys Gly Thr Glu Asp Ser
        195                 200                 205
Gly Thr Thr Val Leu Leu Pro Leu Val Ile Phe Phe Gly Leu Cys Leu
    210                 215                 220
Leu Ser Leu Leu Phe Ile Gly Leu Met Tyr Arg Tyr Gln Arg Trp Lys
225                 230                 235                 240
Ser Lys Leu Tyr Ser Ile Val Cys Gly Lys Ser Thr Pro Glu Lys Glu
                245                 250                 255
Gly Glu Leu Glu Gly Thr Thr Thr Lys Pro Leu Ala Pro Asn Pro Ser
            260                 265                 270
Phe Ser Pro Thr Pro Gly Phe Thr Pro Thr Leu Gly Phe Ser Pro Val
        275                 280                 285
Pro Ser Ser Thr Phe Thr Ser Ser Ser Thr Tyr Thr Pro Gly Asp Cys
    290                 295                 300
Pro Asn Phe Ala Ala Pro Arg Arg Glu Val Ala Pro Pro Tyr Gln Gly
305                 310                 315                 320
Ala Asp Pro Ile Leu Ala Thr Ala Leu Ala Ser Asp Pro Ile Pro Asn
                325                 330                 335
Pro Leu Gln Lys Trp Glu Asp Ser Ala His Lys Pro Gln Ser Leu Asp
            340                 345                 350
Thr Asp Asp Pro Ala Thr Leu Tyr Ala Val Val Glu Asn Val Pro Pro
        355                 360                 365
Leu Arg Trp Lys Glu Phe Val Arg Arg Leu Gly Leu Ser Asp His Glu
    370                 375                 380
Ile Asp Arg Leu Glu Leu Gln Asn Gly Arg Cys Leu Arg Glu Ala Gln
385                 390                 395                 400
Tyr Ser Met Leu Ala Thr Trp Arg Arg Arg Thr Pro Arg Glu Ala
                405                 410                 415
Thr Leu Glu Leu Leu Gly Arg Val Leu Arg Asp Met Asp Leu Leu Gly
            420                 425                 430
Cys Leu Glu Asp Ile Glu Glu Ala Leu Cys Gly Pro Ala Ala Leu Pro
        435                 440                 445
Pro Ala Pro Ser Leu Leu Arg
    450                 455

<210> SEQ ID NO 13
<211> LENGTH: 171
<212> TYPE: PRT
<213> ORGANISM: Artificial
<220> FEATURE:
<223> OTHER INFORMATION: TNFRI171-A2 S92I/H95F/R97P/H98A

<400> SEQUENCE: 13

Asp Ser Val Cys Pro Gln Gly Lys Tyr Ile His Pro Gln Asn Asn Ser
1               5                   10                  15
Ile Cys Cys Thr Lys Cys His Lys Gly Thr Tyr Leu Tyr Asn Asp Cys
                20                  25                  30
Pro Gly Pro Gly Gln Asp Thr Asp Cys Arg Glu Cys Glu Ser Gly Ser
            35                  40                  45
Phe Thr Ala Ile Glu Asn Phe Leu Pro Ala Cys Leu Ser Cys Ser Lys
        50                  55                  60
```

```
Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170

<210> SEQ ID NO 14
<211> LENGTH: 171
<212> TYPE: PRT
<213> ORGANISM: Artificial
<220> FEATURE:
<223> OTHER INFORMATION: TNFRI171-A9 S92M/H95F/R97P/H98A

<400> SEQUENCE: 14

Asp Ser Val Cys Pro Gln Gly Lys Tyr Ile His Pro Gln Asn Asn Ser
1                5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Met Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170

<210> SEQ ID NO 15
<211> LENGTH: 171
<212> TYPE: PRT
<213> ORGANISM: Artificial
<220> FEATURE:
<223> OTHER INFORMATION: TNFRI 171-S36 L68V/S92M/H95F/R97P/H98A

<400> SEQUENCE: 15

Asp Ser Val Cys Pro Gln Gly Lys Tyr Ile His Pro Gln Asn Asn Ser
1                5                  10                  15

Ile Cys Cys Thr Lys Cys His Lys Gly Thr Tyr Val Tyr Asn Asp Cys
            20                  25                  30
```

```
Pro Gly Pro Gly Gln Asp Thr Asp Cys Arg Glu Cys Glu Ser Gly Ser
        35                  40                  45

Phe Thr Ala Met Glu Asn Phe Leu Pro Ala Cys Leu Ser Cys Ser Lys
 50                  55                  60

Cys Arg Lys Glu Met Gly Gln Val Glu Ile Ser Ser Cys Thr Val Asp
65                   70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170

<210> SEQ ID NO 16
<211> LENGTH: 171
<212> TYPE: PRT
<213> ORGANISM: Artificial
<220> FEATURE:
<223> OTHER INFORMATION: TNFRI 171-S54 L68V/S92I/H95F/R97P/H98A/K161N

<400> SEQUENCE: 16

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Glu Asn Phe Leu Pro Ala Cys Leu Ser Cys Ser Lys
 50                  55                  60

Cys Arg Lys Glu Met Gly Gln Val Glu Ile Ser Ser Cys Thr Val Asp
65                   70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Asn Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170

<210> SEQ ID NO 17
<211> LENGTH: 170
<212> TYPE: PRT
<213> ORGANISM: Artificial
<220> FEATURE:
<223> OTHER INFORMATION: TNFRI 171-S57 L68V/S92M/H95F/R97P/H98A/K161N
```

```
<400> SEQUENCE: 17

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Val Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Met Glu Asn Phe Leu Pro Ala Cys Leu Ser Cys Ser Lys
        50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Asn Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr
                165                 170

<210> SEQ ID NO 18
<211> LENGTH: 171
<212> TYPE: PRT
<213> ORGANISM: Artificial
<220> FEATURE:
<223> OTHER INFORMATION: TNFRI 171-S58 L68V/S92M/H95F/R97P/H98A/D207N

<400> SEQUENCE: 18

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Val Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Met Glu Asn Phe Leu Pro Ala Cys Leu Ser Cys Ser Lys
        50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asn Ser Gly Thr Thr
                165                 170
```

-continued

```
<210> SEQ ID NO 19
<211> LENGTH: 171
<212> TYPE: PRT
<213> ORGANISM: Artificial
<220> FEATURE:
<223> OTHER INFORMATION: TNFRI 171-S62 L68V/S92I/H95F/R97P/H98G/K161Q

<400> SEQUENCE: 19
```

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Glu Asn Phe Leu Pro Gly Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170

```
<210> SEQ ID NO 20
<211> LENGTH: 171
<212> TYPE: PRT
<213> ORGANISM: Artificial
<220> FEATURE:
<223> OTHER INFORMATION: TNFRI 171-S63 L68V/S92M/H95F/R97P/H98G/K161N

<400> SEQUENCE: 20
```

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Met Glu Asn Phe Leu Pro Gly Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Asn Gln Asn Thr Val Cys Thr Cys
        115                 120                 125

His Ala Gly Phe Phe Leu Arg Glu Asn Glu Cys Val Ser Cys Ser Asn
    130                 135                 140

```
Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

<210> SEQ ID NO 21
<211> LENGTH: 126
<212> TYPE: PRT
<213> ORGANISM: Artificial
<220> FEATURE:
<223> OTHER INFORMATION: TNFRI126-A2 S92I/H95F/R97P/H98A

<400> SEQUENCE: 21

```
Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Ile Glu Asn Phe Leu Pro Ala Cys Leu Ser Cys Ser Lys
        50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys
            115                 120                 125
```

<210> SEQ ID NO 22
<211> LENGTH: 126
<212> TYPE: PRT
<213> ORGANISM: Artificial
<220> FEATURE:
<223> OTHER INFORMATION: TNFRI126-A9 S92M/H95F/R97P/H98A

<400> SEQUENCE: 22

```
Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Met Glu Asn Phe Leu Pro Ala Cys Leu Ser Cys Ser Lys
        50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys
            115                 120                 125
```

<210> SEQ ID NO 23
<211> LENGTH: 126
<212> TYPE: PRT
<213> ORGANISM: Artificial

<220> FEATURE:
<223> OTHER INFORMATION: TNFRI 126-S36 L68V/S92M/H95F/R97P/H98A

<400> SEQUENCE: 23

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Val Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Met Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125

<210> SEQ ID NO 24
<211> LENGTH: 126
<212> TYPE: PRT
<213> ORGANISM: Artificial
<220> FEATURE:
<223> OTHER INFORMATION: TNFRI 126-S54 L68V/S92I/H95F/R97P/H98A/K161N

<400> SEQUENCE: 24

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Val Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Ile Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Asn Gln Asn Thr Val Cys
        115                 120                 125

<210> SEQ ID NO 25
<211> LENGTH: 126
<212> TYPE: PRT
<213> ORGANISM: Artificial
<220> FEATURE:
<223> OTHER INFORMATION: TNFRI 126-S57 L68V/S92M/H95F/R97P/H98A/K161N

<400> SEQUENCE: 25

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Val Tyr Asn Asp Cys
                20                  25                  30

```
Pro Gly Pro Gly Gln Asp Thr Asp Cys Arg Glu Cys Glu Ser Gly Ser
            35                  40                  45

Phe Thr Ala Met Glu Asn Phe Leu Pro Ala Cys Leu Ser Cys Ser Lys
 50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
                100                 105                 110

Thr Val His Leu Ser Cys Gln Glu Asn Gln Thr Val Cys
            115                 120                 125

<210> SEQ ID NO 26
<211> LENGTH: 126
<212> TYPE: PRT
<213> ORGANISM: Artificial
<220> FEATURE:
<223> OTHER INFORMATION: TNFRI 126-S62 L68V/S92I/H95F/R97P/H98G/K161Q

<400> SEQUENCE: 26

Asp Ser Val Cys Pro Gln Gly Lys Tyr Ile His Pro Gln Asn Asn Ser
 1               5                  10                  15

Ile Cys Cys Thr Lys Cys His Lys Gly Thr Tyr Val Tyr Asn Asp Cys
             20                  25                  30

Pro Gly Pro Gly Gln Asp Thr Asp Cys Arg Glu Cys Glu Ser Gly Ser
            35                  40                  45

Phe Thr Ala Ile Glu Asn Phe Leu Pro Gly Cys Leu Ser Cys Ser Lys
 50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Thr Val Cys
            115                 120                 125

<210> SEQ ID NO 27
<211> LENGTH: 126
<212> TYPE: PRT
<213> ORGANISM: Artificial
<220> FEATURE:
<223> OTHER INFORMATION: TNFRI 126-S63 L68V/S92M/H95F/R97P/H98G/K161N

<400> SEQUENCE: 27

Asp Ser Val Cys Pro Gln Gly Lys Tyr Ile His Pro Gln Asn Asn Ser
 1               5                  10                  15

Ile Cys Cys Thr Lys Cys His Lys Gly Thr Tyr Val Tyr Asn Asp Cys
             20                  25                  30

Pro Gly Pro Gly Gln Asp Thr Asp Cys Arg Glu Cys Glu Ser Gly Ser
            35                  40                  45

Phe Thr Ala Met Glu Asn Phe Leu Pro Gly Cys Leu Ser Cys Ser Lys
 50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95
```

Ser Glu Asn Leu Phe Gln Cys Phe Asn Cys Ser Leu Cys Leu Asn Gly
            100                 105                 110

Thr Val His Leu Ser Cys Gln Glu Asn Gln Asn Thr Val Cys
        115                 120                 125

<210> SEQ ID NO 28
<211> LENGTH: 105
<212> TYPE: PRT
<213> ORGANISM: Artificial
<220> FEATURE:
<223> OTHER INFORMATION: TNFRI105-A2 S92I/H95F/R97P/H98A

<400> SEQUENCE: 28

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
            100                 105

<210> SEQ ID NO 29
<211> LENGTH: 105
<212> TYPE: PRT
<213> ORGANISM: Artificial
<220> FEATURE:
<223> OTHER INFORMATION: TNFRI105-A9 S92M/H95F/R97P/H98A

<400> SEQUENCE: 29

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Met Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
            100                 105

<210> SEQ ID NO 30
<211> LENGTH: 105
<212> TYPE: PRT
<213> ORGANISM: Artificial
<220> FEATURE:
<223> OTHER INFORMATION: TNFRI 105-S36 L68V/S92M/H95F/R97P/H98A

<400> SEQUENCE: 30

-continued

```
Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Val Tyr Asn Asp Cys
            20              25                  30

Pro Gly Pro Gly Gln Asp Thr Asp Cys Arg Glu Cys Glu Ser Gly Ser
        35              40              45

Phe Thr Ala Met Glu Asn Phe Leu Pro Ala Cys Leu Ser Cys Ser Lys
    50              55              60

Cys Arg Lys Glu Met Gly Gln Val Glu Ile Ser Ser Cys Thr Val Asp
65              70              75              80

Arg Asp Thr Val Cys Gly Cys Arg Lys Asn Gln Tyr Arg His Tyr Trp
            85              90              95

Ser Glu Asn Leu Phe Gln Cys Phe Asn
            100             105
```

USES OF MODIFIED HUMAN TUMOR NECROSIS FACTOR RECEPTOR-1 POLYPEPTIDE

CROSS-REFERENCE TO RELATED APPLICATIONS

Figure 1:
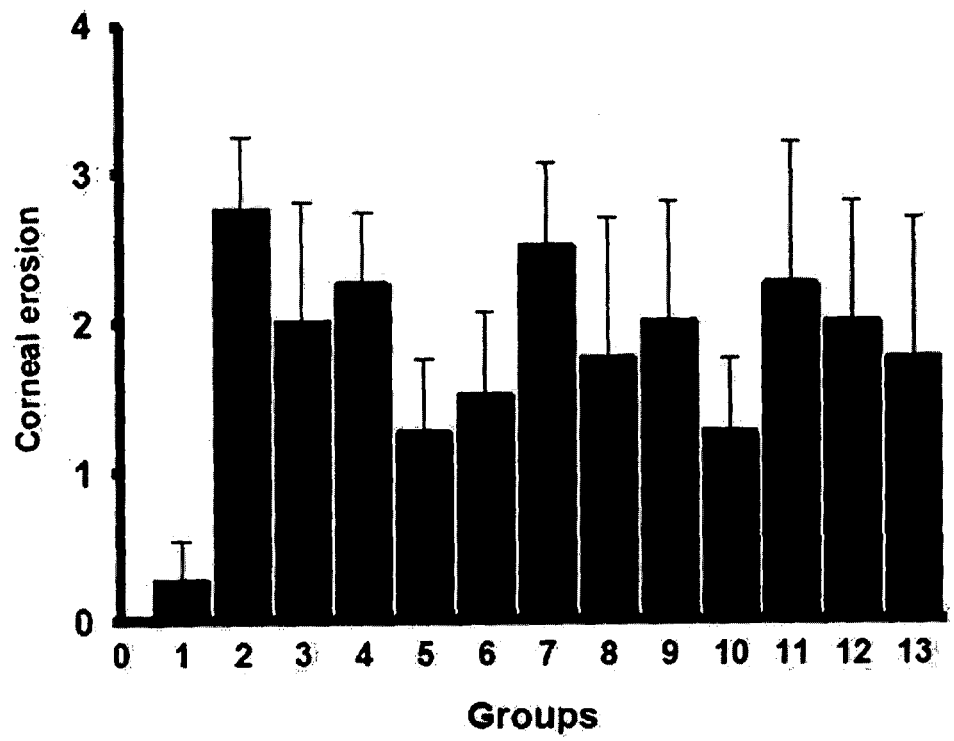

This application is a U.S. national phase under the provisions of 35 U.S.C. §371 of International Patent Application No. PCT/KR13/00983 filed Feb. 7, 2013, which in turn claims priority of Korean Patent Application No. 10-2012-0066527 filed Jun. 21, 2012. The disclosures of such international patent application and Korean priority patent application are hereby incorporated herein by reference in their respective entireties, for all purposes.

TECHNICAL FIELD

The present invention relates to new uses of modified human tumor necrosis factor receptor-1 polypeptides (TNFRI), and more particularly, to uses thereof for prevention and treatment of dry eye syndrome.

BACKGROUND ART

Dry eye syndrome (or 'dry eye'), also called keratoconjunctivitis sicca, is an eye disease that affects millions of people each year. Particularly, this disease is known to be common in women after menopause due to hormonal changes caused by stopping menstruation. The degrees of dry eye syndrome are varied from person to person. Patients with mild symptoms may feel a burning sensation, dryness, and a foreign body sensation, while patients with severe symptoms may have seriously damaged vision. Other diseases such as Sjogren's syndrome and cicatricial pemphigoid, sometimes, also exhibit complex dry eye syndrome.

Based on research results until now, it has been understood that autoimmune response associated with cytokines, antigen-labeled cells, and the like, occur on the ocular surface due to various stress, which causes immune cells to agglomerate on the corneal tissue, resulting in damaging the tissue, and thus induces dry eye syndrome.

As representative treatments of dry eye syndrome, artificial tears are used to complement an ocular tear film or reduce the evaporation of tears to stabilize the tear film. In addition, a tear insert may be used to stimulate the production of tears. A main ingredient of the artificial tear is cellulose ether, carbomer, polyvinyl alcohol, polyvinyl pyrollidone, sodium hyaluronate, or the like, and the artificial tear is prepared by dissolving it in buffer or isotonic saline. These ingredients make the solution viscous to thereby prevent the solution from easily flowing from the eye, prevent the evaporation of tear, and serve as a lubricant. However, these treatments have a limitation in that they are not fundamental treatments but symptomatic treatments.

Meanwhile, as it was discovered that the causes of dry eye are associated with inflammation response on the ocular surface, researches and efforts to apply various kinds of anti-inflammatory materials for treatment were carried out and their effects were proven.

Specifically, it has been reported that ocular tissue such as the lachrymal gland and meibomian gland of patients suffering from dry eye syndromes exhibited unbalanced and excessive inflammation, and it has been known that various compounds, for example, steroids, cytokine secretion inhibitors, cyclosporine A, and 15-HETE, are effective for alleviating the dry eye syndrome.

Tumor necrosis factor alpha (TNFα) is an important factor associated with the inflammation response, and bind to human TNF receptor (TNFR) I or II to thereby induce various cell responses including apoptosis and inflammation response. After it was proven that various autoimmune-related inflammatory diseases can be treated by inhibiting the binding of TNFα and TNFR, various TNFα inhibitors have been developed. Representative examples of TNFα inhibitors may be Etanercept (product name: Enbrel) made from the combination of soluble TNFRII with an FC portion, Infliximab (product name: Remicade) and Adalimumab (product name: Humira), which are antibodies against TNFα, and the like. These are mainly used as treatments for rheumatoid arthritis, psoriasis, Crohn's disease, and the like.

Meanwhile, it has been disclosed that TNFα inhibitors have treatment effects for dry eye (U.S. Pat. No. 6,428,787B, U.S. Pat. No. 6,379,666B, U.S. Pat. No. 6,177,077B, U.S. Pat. No. 6,204,270B, US 2004/0126372A, WO 00/27421A). In addition, US 2009/0098136A discloses that Etanercept and Infliximab have effects in treating the dry eye syndrome in animal models and administration of the two materials in the form of eye drop tends to improve tear breakup time and corneal staining.

However, the demand is still urgent for new treatments for dry eye syndrome showing higher therapeutic efficacy, particularly, new treatments for dry eye syndrome containing a TNFα inhibitor as an effective ingredient.

SUMMARY OF THE INVENTION

The present inventors found that certain types of tumor necrosis factor receptor-1 (TNFRI) variants and fragments thereof exhibited remarkable clinical effects in treating dry eye syndrome, and then completed the present invention. Therefore, the present invention is directed to new uses of a modified human tumor necrosis factor receptor-1 polypeptide or a fragment thereof, particularly, uses for treating dry eye syndrome.

Korean Patent Laid-Open Publication No. 2011-0043485 by the present applicant discloses, as a TNFα inhibitor, modified human tumor necrosis factor receptor-1 polypeptides and fragments thereof, having improved resistance against protease present in the body, and Korean Patent Laid-Open Publication No. 2012-0027666 by the present applicant discloses, as a TNFα inhibitor, modified human tumor necrosis factor receptor-1 polypeptides and fragments thereof, having increased binding strength with TNFα.

With hard work and effort for research after the above patent applications related to new modified tumor necrosis factor receptor-1 polypeptides, the present inventors developed next-generation tumor necrosis factor receptor-1 variants having more improved efficacy than the modified tumor necrosis factor receptor-1 polypeptides (see, Korean Patent Laid-Open Publication No. 2012-0072323), and confirmed that certain ones of the thus developed tumor necrosis factor receptor-1 variants exhibited remarkable clinical effects in the dry eye syndrome.

Particularly, the present inventors confirmed that through animal models, certain variants according to the present invention exhibited remarkable effects in treating the dry eye syndrome, whereas, surprisingly, Etanercept, a representative TNFα inhibitor, had no distinct effect in improving the symptoms of the dry eye syndrome. This fact means that all of the TNFα inhibitors exhibited significant effects in the dry eye syndrome, and proves that only certain variants according to the present invention may be very useful in treating the dry eye syndrome.

As one aspect of the present invention, the present invention provides a composition for prevention and/or treatment of dry eye syndrome containing at least one modified tumor necrosis factor receptor-1 polypeptide or at least one fragment thereof as an effective ingredient, and a method for prevention and/or treatment of the dry eye syndrome using the same.

Prior to a more detailed description of the present invention hereinafter, the terms used herein are defined in order to explain technical features of the present invention more clearly. Unless stated otherwise, the following terms have the meanings as defined below, throughout the specification and the claims of the present invention.

As used herein, the term "full-length human tumor necrosis factor receptor-1" or "full-length human tumor necrosis factor receptor-1 polypeptide" (hereinafter, "TNFRI" or "TNFRI polypeptide") refers to a polypeptide composed of 455 amino acids derived from a human and capable of binding to TNFα. In particular, natural (wild type) TNFRI has an amino acid sequence as set forth in SEQ ID:1.

As used herein, the term "human tumor necrosis factor receptor-1 fragment" or "human tumor necrosis factor receptor-1 polypeptide fragment" (hereinafter, "TNFRI fragment" or "TNFRI polypeptide fragment") refers to a portion of TNFRI, of which an amino acid sequence is 100% identical to a corresponding amino acid sequence of TNFRI and at least one amino acid residue is deleted. In the TNFRI fragment, the deleted amino acid residue(s) may be located at any position of the polypeptide, including the N-terminus, the C-terminus, and an internal portion of TNFRI. The fragment shares at least one biological characteristic, for example, functions as a TNFα inhibitor or treatment efficacy of the dry eye syndrome, with TNFRI. Representative examples of the TNFRI fragment are fragments having 105, 126, 171 amino acid residues extending from the 41st amino acid residue from the TNFRI N-terminus, which are designated as TNFRI105, TNFRI126, and TNFRI171, respectively.

As used herein, the term "TNFRI variant (or mutant)" or "TNFRI variant (or mutant) fragment", "modified TNFRI polypeptide", or "modified TNFRI polypeptide fragment" refers to modified TNFRI or modified TNFRI fragment having less than 100% sequence identity with TNFRI or TNFRI fragment, which is isolated from the natural or recombinant cells as defined below, and the "TNFRI variant (or mutant) fragment" or "modified TNFRI polypeptide fragment" shares one or more biological characteristics, for example, functions as a TNFα inhibitor or treatment efficacy of the dry eye syndrome, with the "TNFRI variant (or mutant)" or "modified TNFRI polypeptide". Generally, the TNFRI variant has an amino acid sequence having approximately 70% or higher sequence identity with wild-type or native TNFRI or the TNFRI fragment. The sequence identity is preferably at least approximately 75%, more preferably at least approximately 80%, still more preferably at least approximately 85%, even more preferably at least approximately 90%, and most preferably at least approximately 95%. A representative modification type of TNFRI is substitution with a different amino acid residue at a particular position.

As used herein, the term "quadruple variant" refers to a variant with mutation at four positions in the amino acid sequence of tumor necrosis factor receptor-1 or human tumor necrosis factor receptor-1 fragment.

As used herein, the term "quintuple variant" refers to a variant with mutation at five positions in the amino acid sequence of tumor necrosis factor receptor-1 or human tumor necrosis factor receptor-1 fragment.

As used herein, the term "sextuple variant" refers to a variant with mutation at six positions in the amino acid sequence of tumor necrosis factor receptor-1 or human tumor necrosis factor receptor-1 fragment.

As used herein, the term "TNFRIm" refers to a TNFRI fragment having an amino acid sequence composed of m amino acid residues extending from the 41st amino acid residue from the N-terminus in an amino acid sequence of TNFRI. For example, the TNFRI105 fragment refers to a TNFRI fragment having a 105-amino acid sequence extending from the 41st amino acid residue from the TNFRI N-terminus. An another example, the TNFRI126 fragment refers to a TNFRI fragment having a 126-amino acid sequence extending from the 41st amino acid residue from the TNFRI N-terminus.

Amino acids present in various amino acid sequences provided herein is expressed by their known 3-letter or 1-letter abbreviations. Nucleotides present in various nucleic acid fragments are designated by the standard single-letter designation used routinely in the art.

As used herein, the symbol "xAz" refers to the substitution of amino acid residue, x with z at position A from the N-terminus (based on the amino acid sequence of TNFRI) in an amino acid sequence of TNFRI or TNFRI fragment. For example, K48Q refers to the substitution of amino acid residue, lysine (Lys) with glutamine (Gln) at position 48 from the N-terminus in the amino acid sequence of TNFRI according to SEQ ID NO: 1.

A modified TNFRI or modified TNFRI fragment, which is an effective ingredient of the composition for prevention and/or treatment of dry eye syndrome according to the present invention, preferably comprises:

an amino acid sequence including modifications of 4 amino acid residues at positions 92, 95, 97 and 98 (quadruple variant);

an amino acid sequence including modifications of 5 amino acid residues at positions 68, 92, 95, 97 and 98 (quintuple variant); or an amino acid sequence including the modifications of 5 amino acid residues at positions 68, 92, 95, 97 and 98, and additional modification of an amino acid residue at position 161 or 207 (sextuple variant), in an amino acid sequence of a natural TNFRI as set forth in SEQ ID NO:1 or an amino acid sequence of a TNFRI fragment.

The amino acid modification maintains or increases binding affinity to TNFα, maintains or increases resistance against protease, as compared with natural TNFRI or TNFRI fragment, and may include all modifications such as insertion, substitution, deletion, and the like. As a representative example, amino acid substitution may be employed. It is obvious to persons with ordinary knowledge in the art to which the present invention pertains (here, 'those skilled in the art") that, as long as increased binding strength can be provided or resistance against protease can be maintained or increased, other chemical modifications of amino acid at a particular position, posttranslational modification, for example, glycosylation by a carbohydrate moiety, acylation (e.g., acetylation or succinylation), methylation, phosphorylation, hasylation, carbamylation, sulfation, prenylation, oxidation, guanidination, amidination, carbamylation (e.g., carbamoylation), trinitrophenylation, nitration, PEGylation, and the like, may be employed.

A modified TNFRI or modified TNFRI fragment, which is an effective ingredient of the composition for prevention and/or treatment of dry eye syndrome according to the present invention, necessarily includes:

substitution of S with I or M at position 92;
substitution of H with F at position 95;
substitution of R with P at position 97; and
substitution of H with A or G at position 98,
and,
preferably further includes at least one substitution selected from:
substitution of L with V at position 68;
substitution of K with Q or N at position 161; and
substitution of D with N at position 207, in an amino acid sequence of a natural TNFRI as set forth in SEQ ID NO:1 or an amino acid sequence of a TNFRI fragment.

In the foregoing modifications, preferably, S is substituted with M at position 92; H is substituted with G at position 98; and K is substituted with N at position 161.

That is, a quadruple variant including: substitution of S with I or M at position 92; substitution of H with F at position 95; substitution of R with P at position 97; and sub-situation of H with A or G at position 98;

a quintuple variant further including substitution of L with V at position 68 in addition to the quadruple variant; or a sextuple variant further including substitution of K with Q or N at position 161 or substitution of D with N at position 207 in addition to the quintuple variant, is preferably used as an effective ingredient of the composition for prevention and/or treatment of dry eye syndrome according to the present invention.

Further, the composition for prevention and/or treatment of dry eye syndrome according to the present invention may comprise more than one of the modified TNFRIs or TNFRI fragments.

As previously defined, the TNFRI fragment refers to a portion of TNFRI, which exhibits a substantially equivalent effect to TNFRI. Particularly, in the present invention, an amino acid sequence composed of amino acid residues 41 to 211 (SEQ ID NO: 2; TNFRI171) of the amino acid sequence of the natural TNFRI as set forth in SEQ ID NO: 1; an amino acid sequence composed of amino acid residues 41 to 166 (SEQ ID NO: 3; TNFRI126) of the amino acid sequence of the natural TNFRI as set forth in SEQ ID NO: 1; and an amino acid sequence composed of amino acid residues 41 to 145 (SEQ ID NO: 4; TNFRI105) of the amino acid sequence of the natural TNFRI as set forth in SEQ ID NO: 1. For reference, it is known that the fourth domain of TNFRI is not essential for binding with TNFα, and the deletion of the second and third domains causes the loss of binding activity with TNFα (Corcoran et al, *Eur. J. Biochem.* 233:831-840 1994), and it is also well known that a certain moiety of the third domain in the binding of TNFRI and TNFα may be deficient, and the amino acid sequence composed of amino acid residues 59 to 143 of natural TNFRI (SEQ ID NO: 1) alone exhibits biological activity of TNFRI (see, U.S. Pat. No. 6,989,147 or the like).

It is obvious to those skilled in the art that a polypeptide substantially identical to the modified TNFRI or modified TNFRI fragment is also included within the range of the modified TNFRI or modified TNFRI fragment of the present invention. The term "polypeptide substantially identical to the modified TNFRI or modified TNFRI fragment" refers to a polypeptide including substitution, deletion, addition, or other modifications of amino acid residues while the number of amino acid residues with modification and the kind of modification are not particularly limited as long as inherent characteristics of the modified TNFRI or modified TNFRI fragment can be maintained.

In particular, the "polypeptide substantially identical to the modified TNFRI or modified TNFRI fragment" preferably has amino acid modifications for increasing binding affinity to TNFα and/or maintaining/improving resistance against protease, at the positions of residues identified to be functionally unchangeable based on the sequence alignment with the amino acid sequence of the modified TNFRI or modified TNFRI fragment. Those skilled in the art can identify corresponding residues by aligning the amino acid sequence of the TNFRI polypeptide and using conserved and identical amino acid residues as a guide.

Also, the "polypeptide substantially identical to the modified TNFRI or modified TNFRI fragment" may include a polypeptide with modifications even at positions of residues capable of affecting functions of the modified TNFRI or modified TNFRI fragment according to the present invention, so long as characteristics desired by the present invention can be maintained, for example, conservative substitution or the like.

Preferably, the "polypeptide substantially identical to the modified TNFRI or modified TNFRI fragment" may have more than 90%, more than 95%, more than 96%, more than 97%, more than 98%, or more than 99% sequence homology with the polypeptide having the sequence as set forth in SEQ ID NO: 1, except amino acid modifications at the specific positions of the present invention, and may include allelic variant isoforms, tissue-specific isoforms, and allelic variants thereof, synthetic variants having at least one amino acid mutation, substitution, deletion, insertion or addition, synthetic molecules prepared by translating nucleic acids, proteins isolated from human and non-human tissue and cells, chimeric TNFRI polypeptides and modified forms thereof.

Also, a polymeric polypeptide (or referred to as "polypeptide complex") including at least two of the foregoing modified TNFRIs or modified TNFRI fragments is included within the range of the modified TNFRI or modified TNFRI fragment of the present invention.

The polypeptide complex has the structure that at least two modified TNFRI or modified TNFRI fragment are linked, preferably, by covalent bond.

As a preferable embodiment of the present invention, the composition of the present invention comprising at least one modified TNFRI or modified TNFRI fragment having an amino acid sequence selected from below as an effective ingredient:

an amino acid sequence including amino acid modification selected from
S92I/H95F/R97P/H98A, S92M/H95F/R97P/H98A, L68V/S92M/H95F/R97P/H98A, L68V/S92I/H95F/R97P/H98A/K161N, L68V/S92M/H95F/R97P/H98A/K161N, L68V/S92M/H95F/R97P/H98A/D207N, L68V/S92I/H95F/R97P/H98G/K161Q, and L68V/S92M/H95F/R97P/H98G/K161N in the amino acid sequence of natural TNFRI set forth in SEQ ID NO: 1 (TNFRI);

an amino acid sequence including amino acid modification selected from
S92I/H95F/R97P/H98A, S92M/H95F/R97P/H98A, L68V/S92M/H95F/R97P/H98A, L68V/S92I/H95F/R97P/H98A/K161N, L68V/S92M/H95F/R97P/H98A/K161N, L68V/S92M/H95F/R97P/H98A/D207N, L68V/S92I/H95F/R97P/H98G/K161Q, and L68V/S92M/H95F/R97P/H98G/K161N in an amino acid sequence composed of amino acid residues 41 to 211 of the amino acid sequence of the natural TNFRI set forth in SEQ ID NO: 1 (TNFRI171);

an amino acid sequence including amino acid modification selected from

S92I/H95F/R97P/H98A, S92M/H95F/R97P/H98A, L68V/S92M/H95F/R97P/H98A, L68V/S92I/H95F/R97P/H98A/K161N, L68V/S92M/H95F/R97P/H98A/K161N, L68V/S92I/H95F/R97P/H98G/K161Q, and L68V/S92M/H95F/R97P/H98G/K161N in an amino acid sequence composed of amino acid residues 41 to 166 of the amino acid sequence of the natural TNFRI set forth in SEQ ID NO: 1 (TNFRI126); and an amino acid sequence including amino acid modification selected from S92I/H95F/R97P/H98A, S92M/H95F/R97P/H98A and L68V/S92M/H95F/R97P/H98A in an amino acid sequence composed of amino acid residues 41 to 145 of the amino acid sequence of the natural TNFRI set forth in SEQ ID NO: 1 (TNFRI105).

As a more preferable embodiment of the present invention, the composition of the present invention comprises at least one modified TNFRI or modified TNFRI fragment having an amino acid sequence selected from below as an effective ingredient:

an amino acid sequence including amino acid modification selected from

L68V/S92I/H95F/R97P/H98A/K161N, L68V/S92M/H95F/R97P/H98A/D207N and L68V/S92M/H95F/R97P/H98G/K161N in the amino acid sequence of the natural TNFRI set forth in SEQ ID NO: 1 (TNFRI);

an amino acid sequence including amino acid modification selected from

L68V/S92I/H95F/R97P/H98A/K161N, L68V/S92M/H95F/R97P/H98A/D207N, and L68V/S92M/H95F/R97P/H98G/K161N in the amino acid sequence composed of amino acid residues 41 to 211 of the amino acid sequence of the natural TNFRI set forth in SEQ ID NO: 1 (TNFRI171); and an amino acid sequence including amino acid modification selected from L68V/S92I/H95F/R97P/H98A/K161N and L68V/S92M/H95F/R97P/H98G/K161N in the amino acid sequence composed of amino acid residues 41 to 166 of the amino acid sequence of the natural TNFRI set forth in SEQ ID NO: 1 (TNFRI126).

As a most preferable embodiment of the present invention, the composition of the present invention comprises at least one modified TNFRI or modified TNFRI fragment having an amino acid sequence selected from below as an effective ingredient:

an amino acid sequence including amino acid modification selected from

L68V/S92M/H95F/R97P/H98G/K161N and L68V/S92M/H95F/R97P/H98A/D207N in the amino acid sequence of the natural TNFRI set forth in SEQ ID NO: 1 (TNFRI);

an amino acid sequence including amino acid modification selected from

L68V/S92M/H95F/R97P/H98G/K161N and L68V/S92M/H95F/R97P/H98A/D207 in the amino acid sequence composed of amino acid residues 41 to 211 of the amino acid sequence of the natural TNFRI set forth in SEQ ID NO: 1 (TNFRI171); and an amino acid sequence including amino acid modification of L68V/S92M/H95F/R97P/H98G/K161N in the amino acid sequence composed of amino acid residues 41 to 166 of the amino acid sequence of the natural TNFRI set forth in SEQ ID NO: 1 (TNFRI126).

As another preferable embodiment of the present invention, the composition of the present invention comprising at least one modified TNFRI or modified TNFRI fragment having an amino acid sequence selected from SEQ ID NOs: 5 to 30, as an effective ingredient.

The modified TNFRI or modified TNFRI fragment of the present invention may be prepared by using a microorganism such as *E. coli*, yeast, or the like, or an animal cell. These polypeptides and preparation thereof are known in the art, and particularly, described in detail in Korean Patent Laid-Open Publication NO. 2012-0027666.

In addition, the modified TNFRI or modified TNFRI fragment has additional modification for production in a microorganism such as *E. coli*, yeast, or the like, or an animal cell. Preferably, the modified TNFRI or modified TNFRI fragment has a signal sequence or methionine added to the amino terminus of an amino acid sequence thereof.

Further, the present invention provides a gene encoding the modified TNFRI or modified TNFRI fragment; a vector including the gene; or a microorganism or an animal cell transformed with the vector, and also provides a method for producing modified TNFRI or modified TNFRI fragment using the gene, vector, and microorganism or animal cell.

Further, the present invention provides a composition for prevention or treatment for dry eye syndrome comprising a gene encoding the modified TNFRI or modified TNFRI fragment; and a vector including the gene.

Herein, the dry eye syndrome, also called keratoconjunctivitis sicca, is widely defined, including dry eye resulting from:

Stevens-Johnson syndrome, Sjogren's syndrome, ocular cicatricial pemphigoid, blepharitis, corneal damage, infection, Lily-Day syndrome, congenital anodontia, nutritional disturbances or deficiencies (including vitamin), drug side effects, ocular stress, gland and cell damage, smog, tobacco, environmental exposure to very dry air, anemochoric dust, autoimmune and other immune deficiency disorders and dry eye due to aging.

Generally, the dosage of the modified TNFRI or modified TNFRI fragment of the present invention, used for treatment or prevention of dry eye syndrome may be varied depending on the kind, age, and weight of subject to be administered, severity of the symptom, desired treatment effect, administrating method, treatment period, and the like, and the pharmaceutically effective amount for removing or improving dry eye syndrome may be used. As used herein, the term "pharmaceutically effective amount" refers to the amount which improves dry eye syndrome. Generally, in the case of systemic administration, the dosage is about 0.0001~1000 mg, and preferably 0.001~500 mg, which is administered in a single dosage or divided dosages of two to four times per day or administered in a delayed manner. In particular, in the case of topical application to the eye, a medicine containing 0.001~10.0 w/v % and preferably 0.01~10.0 w.v % of the modified TNFRI or modified TNFRI fragment of the present invention is applied to the eye several times per day, and preferably dropped to the eye once to six times per day. However, the application of the medicine is not limited thereto, and it is obvious that those skilled in the art can control an appropriate dosage, an administration interval, and the like, in consideration of various factors.

The composition of the present invention may further comprise physiologically compatible vehicles and/or additives, which are generally selectable in the art, in addition to the modified TNFRI or modified TNFRI fragment of the present invention. The composition according to the present invention may further comprise, as the vehicles and/or additives, an isotonicity agent, a buffer, a surfactant, a stabilization polymer, a preservative, a viscosity increasing agent, antioxidant, and the like, but is not limited thereto. It is obvious to those skilled in the art that other components conventionally used may be further included. In addition, the composition of the present invention may further comprise a surfactant and/or a mitigating agent and/or a stabilization polymer.

The isotonicity agent is used to adjust tonicity of the composition, preferably tonicity of natural tears used as an ophthalmic composition. For example, the tonicity of the composition may be adjusted similarly to physiological isotonicity by adding sodium chloride, potassium chloride, magnesium chloride, calcium chloride, simple sugars, such as dextrose, fructose, and galactose, and/or simple polyols, such as sugar alcohol, mannitol, sorbitol, xylitol, lactitol, isomalt, and maltitol, or hydrogenated starch hydrolysate to the composition. The amount of this isotonicity agent may be appropriately selected depending on the specific kind of reagent.

As the buffer, at least one selected from for example sodium phosphate, sodium acetate, sodium citrate, sodium borate, and boric acid may be used. The buffer may be used to prevent pH change of the composition under storage conditions. The concentration of the buffer is varied depending on the kind of reagent, but may be selected so as to maintain a pH value of 5 to 8, and more preferably 5 to 7.

The surfactant is used to dissolve effective ingredients and stabilize a colloidal dispersion, e.g., a micelle solution, a microemulsion, emulsion, or a suspension. For example, polysorbate, poloxamer, polyoxyl 40 stearate, polyoxyl caster oil, tyloxapol, triton (e.g., Triton X114), and sorbitan monolaurate may be used.

As the stabilization polymer, a polyelectrolyte selected from cross-linked polyacrylates, for example, carbomer or Pemulen (product name), specifically, 0.1 to 0.5% (w/w) of carbomer 974P (polyacrylic acid) may be used.

The preservant is used to prevent microorganism contamination during use of the composition, and for example, benzalkonium chloride, chlorobutanol, benzodedecynium bromide, methyl paraben, propyl paraben, phenylethyl alcohol, edentate disodium, sorbic acid, polyquarternium-1, or other agents known in the art may be used.

The viscosity increasing agent is used to increase viscosity of a carrier, and examples thereof may include polysaccharides, such as hyaluronic acid and its salts, chondroitin sulfate and its salts, various polymers of dextrans and celluloses; vinyl polymers; acrylic acid polymers, but are not limited thereto.

The antioxidant may be further added to the composition of the present invention to prevent active ingredients from being oxidized during storage. Examples of the antioxidant may include vitamin E and its analogs, ascorbic acid and its derivatives, and butylated hydroxyanisole (BHA).

The modified TNFRI or modified TNFRI fragment used in the present invention is formulated into a pharmaceutical preparation for application to a human or animal, and may be systemically or topically administered by oral administration, intravenous administration, subcutaneous administration, rectal or vaginal administration, or administration to a tropical region (eye). Preferably, tropical administration to the eye may be employed in consideration of systemic influence, significant expression of effects, and the like.

When the modified TNFRI or modified TNFRI fragment is formulated, it may be administered in a formulation form generated by the conventional methods. The administration form may be, for example, eye drop, eye ointment, powder, granule, tablet, capsule, injection, ointment, and the like, and eye drop and eye ointment may be preferable. These preparations may be produced by general methods known in the art. As the ophthalmic tropical administration form, a drop, spray, or gel type is possible, and as another administration form, administration to the eye using liposome may be used. Alternatively, injection to the tear film through a pump-catheter system may be used. As another embodiment, a continuous or selective releasing apparatus, for example, a system such as the Ocusert (trademark name) system (Alza Corp., Palo Alto, Calif.) may be used. As a further embodiment, the TNFRI variant may be included in a contact lens on the eye, and may be transferred thereby or attached thereto. As still another embodiment, the TNFRI variant may be used while contained with a sponge or a cotton swab applicable to the ocular surface, or as a liquid spray applicable to the ocular surface. As still another embodiment, the modified TNFRI or modified TNFRI fragment of the present invention may be directly injected onto the ocular surface or the lacrimal tissue.

In addition to the topical administration method, the modified TNFRI or modified TNFRI fragment of the present invention may be systemically administered by various methods. As one example, there is an aerosol suspension of inhalable particles. The modified TNFRI or modified TNFRI fragment of the present invention may be absorbed into the blood through the lung, contacted to the lacrimal tissue through the nasal lacrimal duct, or contacted with the lacrimal gland in a pharmaceutically effective amount. As another method, nasal spray of inhalable particles, nasal drops of liquid formulations, or administration of a liquid/liquid suspension in an eye washing or eye drop type may be possible. The composition for nasal spray and nasal or eye drop may be prepared by being blended with an appropriate vehicle such as a sterilized saline solution or sterile pyrogen free water through technologies known in the art.

The modified TNFRI or modified TNFRI fragment of the present invention may be administered to tissue by oral administration, and may be used in a form of tablet, lozenge, aqueous or oily suspension, dispersible powder or granule, emulsion, hard or soft capsule, syrup, or elixir. An oral composition may be prepared by the methods known in the field of pharmaceutical manufacturing.

Alternatively, the modified TNFRI polypeptide or its fragment of the present invention may be directly dropped in a form of gel, cream, or liquid suspension, during the operation.

Besides the above descriptions, those skilled in the art will make appropriate modifications and applications of the embodiments of the invention from the descriptions of the present specification, which are also included in the scope of the invention.

BRIEF DESCRIPTION OF DRAWINGS

FIG. 1 shows corneal damage recovery effects by TNFRI variants.

Lane 1: normal group, Lane 2: induction of dry eye+ vehicle (topical administration), Lane 3: induction of dry eye+Etanercept (2.5 mg/ml, topical administration), Lane 4: induction of dry eye+HL036335 (2.5 mg/ml, topical administration), Lane 5: induction of dry eye+HL036337 (2.5 mg/ml, topical administration), Lane 6: induction of dry eye+HL036326 (2.5 mg/ml, topical administration), Lane 7: induction of dry eye+HL036222 (2.5 mg/ml, topical administration), Lane 8: induction of dry eye+HL036329 (2.5 mg/ml, topical administration), Lane 9: induction of dry eye+HL036304 (2.5 mg/ml, topical administration), Lane 10: induction of dry eye+HL036330 (2.5 mg/ml, topical administration), Lane 11: induction of dry eye+HL036229 (2.5 mg/ml, topical administration), Lane 12: induction of dry eye+HL036402 (2.5 mg/ml, topical administration), Lane 13: induction of dry eye+Cyclosporine A (0.05%, topical administration)

Figure 2:
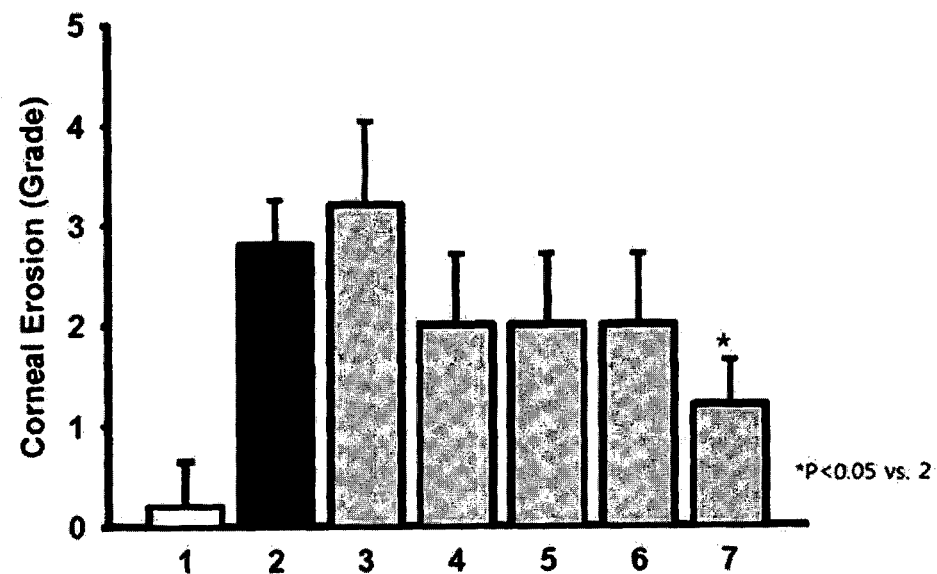

FIG. 2 shows corneal damage recovery effects according to the concentrations of TNFRI variants.

Lane 1: normal group, Lane 2: induction of dry eye, Lane 3: induction of dry eye+Etanercept (5 mg/kg, subcutaneous administration), Lane 4: induction of dry eye+HL036337 (0.5 mg/kg, subcutaneous administration), Lane 5: induction of dry eye+HL036337 (5 mg/kg, subcutaneous administration), Lane 6: induction of dry eye+HL036337 (0.625 mg/ml, topical administration), Lane 7: induction of dry eye+HL036337 (6.25 mg/ml, topical administration)

Figure 3:
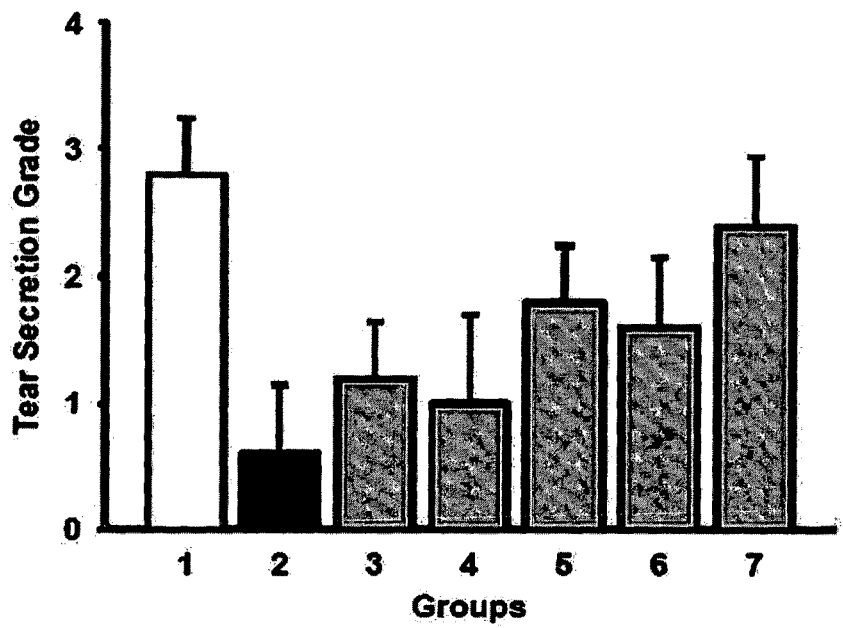

FIG. 3 shows tear volume increase effects by TNFRI variants.

Lane 1: normal group, Lane 2: induction of dry eye, Lane 3: induction of dry eye+Etanercept (5 mg/kg, subcutaneous administration), Lane 4: induction of dry eye+HL036337 (0.5 mg/kg, subcutaneous administration), Lane 5: induction of dry eye+HL036337 (5 mg/kg, subcutaneous administration), Lane 6: induction of dry eye+HL036337 (0.625 mg/ml, topical administration), Lane 7: induction of dry eye+HL036337 (6.25 mg/ml, topical administration)

Figure 4:
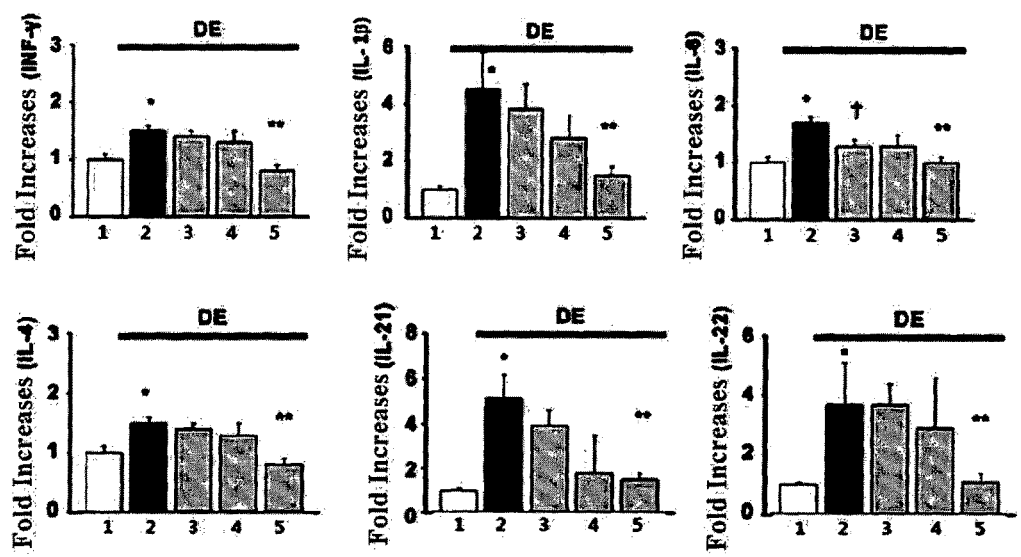

FIG. 4 shows anti-inflammatory effects in the cornea by TNFRI variants.

Lane 1: normal group, Lane 2: induction of dry eye, Lane 3: induction of dry eye+Etanercept (5 mg/kg, subcutaneous administration), Lane 4: induction of dry eye+HL036337 (5 mg/kg, subcutaneous administration), Lane 5: induction of dry eye+HL036337 (6.25 mg/ml, topical administration)

Figure 5:
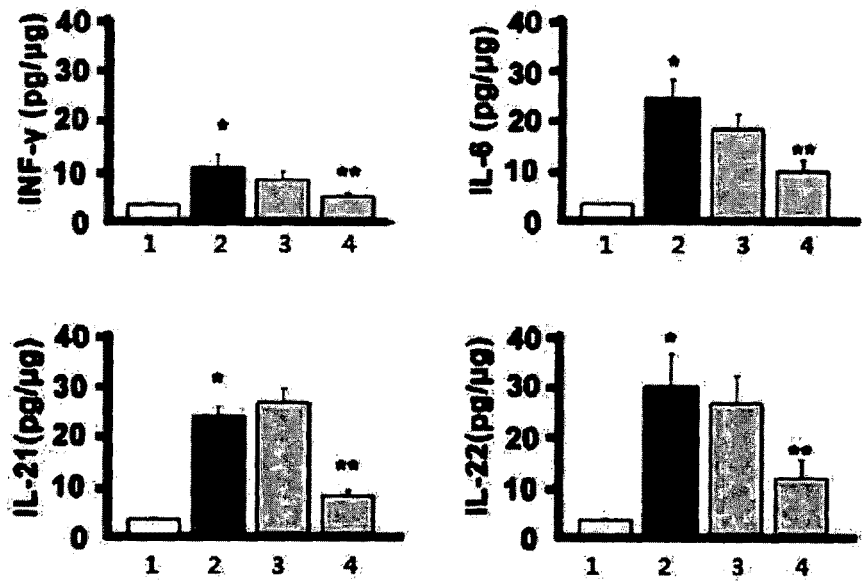

FIG. 5 shows anti-inflammatory effects on the ocular surface by TNFRI variants.

Lane 1: normal group, Lane 2: induction of dry eye, Lane 3: induction of dry eye+Etanercept (5 mg/kg, subcutaneous administration), Lane 4: induction of dry eye+HL036337 (6.25 mg/ml, topical administration)

Figure 6:
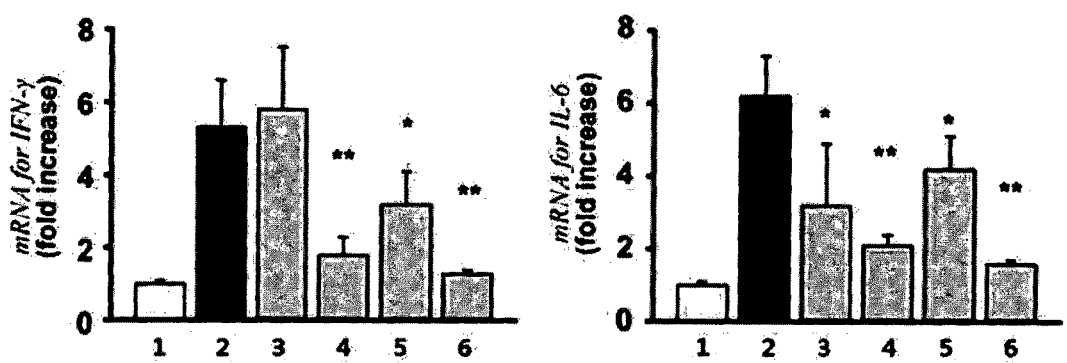

FIG. 6 shows anti-inflammatory effects in the lacrimal gland by TNFRI variants.

Lane 1: normal group, Lane 2: induction of dry eye+ Vehicle (topical administration), Lane 3: induction of dry eye+Etanercept (0.25%, topical administration), Lane 4: induction of dry eye+HL036337 (0.25%, topical administration), Lane 5: induction of dry eye+Cyclosporine A (0.05%, topical administration), Lane 6: induction of dry eye+Methylprednisolone (0.1%, topical administration)

DETAILED DESCRIPTION AND PREFERRED EMBODIMENTS OF THE INVENTION

Various advantages and features of the present invention and methods for accomplishing them will become apparent from the preparative examples, examples, and experimental examples below. However, these are provided merely for better understanding of the present invention, and the present invention is not limited by the examples disclosed below.

Preparative Example Preparation of TNFRI Fragment Variant (1) Design of TNFRI Variant From Korean Patent Application No. 2010-0089395 (Laid-Open Publication No. 2012-0027666) and Korean Patent Application No. 2011-0138751 (Laid-Open Publication No. 2012-0072323), modified TNFRI ("TNFRI variants") having amino acid modifications of Table 1 below were selected as candidates.

TABLE 1

TNFRI variants of the present invention

| Code Number | TNFRI variants ID. | Modification |
| --- | --- | --- |
| HL036222 | TNFRIm-A2 | S92I, H95F, R97P, H98A |
| HL036229 | TNFRIm-A9 | S92M, H95F, R97P, H98A |
| HL036304 | TNFRIm-S36 | L68V, S92M, H95F, R97P, H98A |
| HL036326 | TNFRIm-S54 | L68V, S92I, H95F, R97P, H98A, K161N |
| HL036329 | TNFRIm-S57 | L68V, S92M, H95F, R97P, H98A, K161N |
| HL036330 | TNFRIm-S58 | L68V, S92M, H95F, R97P, H98A, D207N |
| HL036335 | TNFRIm-S62 | L68V, S92I, H95F, R97P, H98G, K161Q |
| HL036337 | TNFRIm-S63 | L68V, S92M, H95F, R97P, H98G, K161N |
| HL036402 | TNFRIm-WT | None (wild type) |

("m" means 105, 126 or 171)

For the preparation of the TNFRI variants, genetic information of human TNFRI that has already been disclosed was used. Amino acid sequences of TNFRI171, TNFRI126, and TNFRI105 variant polypeptides, to which modifications of Table 1 above were applied, were set forth in SEQ ID NOs: 13 to 30 (excluding a wild type).

(2) Preparation of DNA Encoding TNFRI Variant

For the construction of site-specific TNFRI variants, the TNFRI variants were constructed by site-directed mutagenesis. Primers and templates used to construct the TNFRI variants having amino acid modifications described in Table 1 above were shown in Table 2 below.

Specifically, using the TNFRI plasmid as a template, 20 pmole of each pair of primers of Table 2 below were dissolved in distilled water, followed by PCR using Pfu polymerase, to thereby construct each site-directed variant.

A TNFRI171 fragment gene and, TNFRI expression vectors, TNFRI105, TNFRI126, and TNFRI171 expression vectors, for constructing the TNFRI variants, were construcutued according to the disclosure of Korean Patent Laid-Open Publication No. 2012-0027666.

For constructing plasmids encoding TNFRI105-A30, TNFRI-126-A30, and TNFRI-171-A30, respective amplification reactions were carried out by employing primers corresponding to A30 of Table 2 and using the constructed pET44a-Met-TNFRI105, pET44a-Met-TNFRI126, and pET44a-Met-TNFRI171 plasmid as templates (the thus obtained plasmids refer to pET-TNFRI105_A30, pET-TNFRI126_A30, and pETTNFRI171_A30, respectively, and descriptions of the lengths of amino acid sequences are omitted). Then, as shown in Table 2 below, pET-TNFRI_A2 and pET-TNFRI_A9 were constructed by the same method while employing primers corresponding to A2 and A9 and using the thus constructed plasmids as templates. Other plasmids were constructed by the same method while employing primers of Table 2 and using the thus constructed plasmids as templates.

TABLE 2

Information of primer for site-directed mutagenesis

| Mutation number | PCR template | primer sequence |
|---|---|---|
| A2 (pET-TNFRI_A2) | pET-TNFRI_A30 | 5'-GTCATTTACAGCGATTGAGAATTTTCTGCCGGC-3'<br>5'-GCCGGCAGAAAATTCTCAATCGCTGTAAATGAC-3' |
| A9 (pET-TNFRI_A9) | pET-TNFRI_A2 | 5'-GGGTCATTTACAGCGATGGAGAATTTTCTGC-3'<br>5'-GCAGAAAATTCTCCATCGCTGTAAATGACCC-3' |
| A21 (pET-TNFRI_A21) | pET-TNFRI_A2 | 5'-GAGAATTTTCTGCCGGGGTGCCTGAGCTGTTCTA-3'<br>5'-TAGAACAGCTCAGGCACCCCGGCAGAAAATTCTC-3' |
| A22 (pET-TNFRI_A22) | pET-TNFRI_A9 | 5'-GAGAATTTTCTGCCGGGGTGCCTGAGCTGTTCTA-3'<br>5'-TAGAACAGCTCAGGCACCCCGGCAGAAAATTCTC-3' |
| A30 (pET-TNFRI_A30) | pET44a-Met-TNFRI105, pET44a-Met-TNFRI126, or pET44a-Met-TNFRI171 | 5'-GAGTGGGTCATTTACAGCGATTCCGAATTTTCTGCCGGCGTGCCTGAGCTGTTCTAAG-3'<br>5'-CTTAGAACAGCTCAGGCACGCCGGCAGAAAATTCGGAATCGCTGTAAATGACCCACTC-3' |
| S31 (pET-TNFRI_S31) | pET-TNFRI_A2 | 5'-CACAAAGGGACGTACGTGTATAATGACTGTCCG-3'<br>5'-CGGACAGTCATTATACACGTACGTCCCTTTGTG-3' |
| S36 (pET-TNFRI _S36) | pET-TNFRI_A9 | 5'-CACAAAGGGACGTACGTGTATAATGACTGTCCG-3'<br>5'-CGGACAGTCATTATACACGTACGTCCCTTTGTG-3' |
| S46 (pET-TNFRI_ S46) | pET-TNFRI_A21 | 5'-GAGAATTTTCTGCCGGGGTGCCTGAGCTGTTCTA-3'<br>5'-TAGAACAGCTCAGGCACCCCGGCAGAAAATTCTC-3' |
| S47 (pET-TNFRI_S47) | pET-TNFRI_A22 | 5'-GAGAATTTTCTGCCGGGGTGCCTGAGCTGTTCTA-3'<br>5'-TAGAACAGCTCAGGCACCCCGGCAGAAAATTCTC-3' |
| S54 (pET-TNFRI_S54) | pET-TNFRI_S31 | 5'-CTGTCCTGTCAGGAGAACCAGAATACAGTTTGTA-3'<br>5'-TACAAACTGTATTCTGGTTCTCCTGACAGGACAG-3' |
| S57 (pET-TNFRI_S57) | pET-TNFRI_S36 | 5'-CTGTCCTGTCAGGAGAACCAGAATACAGTTTGTA-3'<br>5'-TACAAACTGTATTCTGGTTCTCCTGACAGGACAG-3' |
| S58 (pET-TNFRI_S58) | pET-TNFRI_S36 | 5'-ATGTTAAGGGCACTGAGAACTCAGGCACCACATA-3'<br>5'-TATGTGGTGCCTGAGTTCTCAGTGCCCTTAACAT-3' |
| S62 (pET-TNFRI _S62) | pET-TNFRI_S46 | 5'-ATCTGTCCTGTCAGGAGCAGCAGAATACAGTTTG-3'<br>5'-CAAACTGTATTCTGCTGCTCCTGACAGGACAGAT-3' |
| S63 (pET-TNFRI_S63) | pET-TNFRI_S47 | 5'-CTGTCCTGTCAGGAGAACCAGAATACAGTTTGTA-3'<br>5'-TACAAACTGTATTCTGGTTCTCCTGACAGGACAG-3' |

50.0 µl of a reaction solution was prepared by using 1.0 µl of each template plasmid DNA, 1.0 µl of 20 pmole N-primers, 1.0 µl of 20 pmole C-primers, 25.0 µl of 2× PrimeSTAR PCR buffer, 4.0 µl of 200 µM dNTP, 0.5 µl of PrimeSTAR HS DNA polymerase (Takara, Cat. No: R044A), and 17.5 µl of distilled water, and then was used for the above amplification reaction.

PCR was carried out including: primary denaturation at 98° C. for 5 minutes, secondary denaturation at 98° C. for 30 seconds, primer annealing at 55° C. for 30 seconds and elongation at 72° C. for 9 minutes. The process described above, steps of from secondary denaturation to elongation was repeated 17 times (17 cycles) and then the final enzymatic reaction at 72° C. for 10 minutes.

The PCR product was treated with the DpnI enzyme at 37° C. for 2 hours to degrade the *E. coli*-derived DNA and obtain the PCR-amplified DNA. 2 μl of the DNA solution was taken, and then introduced to XL1-blue competent cells (Cat. No: RH119-J80, RBC), which was then transformed by applying heat shock at 42° C. for 1 minute, followed by static culture in an LB solid medium containing ampicillin, to obtain a colony. The colony was cultured in an LB liquid medium containing ampicillin, and then the plasmid was isolated and subjected to nucleotide sequencing analysis to confirm the completion of site-specific mutation.

(3) Production of Biologically Active TNFRI and TNFRI Variants in *E. coli*

(A) Expression of TNFRI and TNFRI Variants

1 μl of the plasmid solution constructed by the above preparative example was taken, and then introduced to BL21Star (DE3) competent cells (Invitrogen, Cat. No: C6010-03), which was then transformed by applying heat shock at 42° C. for 1 minute, followed by static culture in an LB solid medium containing ampicillin, to obtain a colony. *E. coli* BL21Star (DE3) containing the expression vector therein was inoculated onto 50 mL of a YP medium (yeast extract: Merck, Cat. No: 103753, peptone: BD, Cat. No: 243620, and NaCl: Merck, Cat. No: 1064049025) containing 100 μg/ml ampicillin, followed by aeration-culture at 37° C. for 16 hours. The cultured medium was inoculated onto 250 mL of a YP medium containing 100 μg/ml ampicillin to an absorbance value at 600 nm of 0.1 in a 1 L-flask. When the cells were cultured at 37° C. to an absorbance value of 3~4, IPTG was added to reach a final concentration of 1.0 mM, to thereby induce expression. After induction of expression, aeration culture was continued at 37° C. for 3 hours, and then the cells were collected by centrifugation at 6,000 rpm for 20 minutes.

(B) Recovery of Insoluble TNFRI and TNFRI Variant

The collected cells were resuspended in a resuspension solution (50 mM Tris, 0.5 mM EDTA (pH 8.5)). The suspended cells were disrupted with a sonicator (Sonics, Cat. No: VCX 750). After cell disruption, centrifugation at 8000×g was carried out at 10° C. for 30 minutes. The supernatant was discarded and the precipitated pellet was suspended in washing solution 1 (50 mM Tris, 10 mM EDTA, 0.5% Triton X-100 (pH 8.0)), followed by centrifugation at 8000×g and 10° C. for 20 minutes. The supernatant was discarded and the resulting pellet was resuspended in the resuspension solution, followed by centrifugation at 8000×g and 10° C. for 20 minutes. The washed pellet was used immediately, or freeze-stored at ?80° C.

(C) Solubilization and Refolding of TNFRI and TNFRI Variant

The thus obtained pellet was solubilized in 6 mL of a denaturation solution (6~8 M urea or 6~8 M guanidine-HCl, 10 mM dithiothreitol (DTT), 2.0 mM EDTA, and 0.2 M NaCl). Then, the insoluble pellet was filtered off by using a 0.45 μm-syringe filter. The pellet-solubilized solution was 20-fold diluted in a refolding solution (50 mM Tris, 1.0 mM EDTA, 0.5 M L-arginine, 6.0 mM GSH, 4.0 mM GSSG, 240 mM NaCl, 10 mM KCl (pH 9.0)) and gently stirred at 4° C. for 12~24 hours, to induce refolding.

(D) Purification of Refolded TNFRI and TNFRI Variant

In order to purify the refolded TNFRI and TNFRI variants, the refolding solutions were 20-fold concentrated by using a 3 kD Amicon Ultra (Millipore, Cat. No: UFC900324). Then, purification was carried out by using gel permeation chromatography (GPC) using a Superdex 75 prep grade resin (GE)-packed XK25/70 column (GE, Cat. No: 19-0146-01).

Specifically, before the refolded sample was loaded on the column, the column was equilibrated with 4~5 column volumes of an equilibration solution (50 mM sodium phosphate, 100 mM NaCl (pH 7.0)). After 2 mL of the sample was loaded on the column, the equilibration solution was allowed to flow through the column at a flow rate of 5 ml/min, and every 5 mL fraction of the sample was collected. The collected samples were analyzed by SDS-PAGE, and then only fractions having purity of 90% or higher were taken. Through the above procedure, TNFRI105, TNFRI126, and TNFRI171 and a TNFRI105 variant, TNFRI126 variant, and TNFRI171 variant, which have Met added to amino terminuses thereof, were purified.

EXAMPLES

Example 1

Verification of Effect of TNFRI Variants on Dry Eye Syndrome Treatment

In order to verify the treatment effect due to TNFα inhibition in the dry eye syndrome treatment, TNFα inhibitors were administered to a dry eye syndrome animal model using mice. Etanercept and TNFRI variants were used as the TNFα inhibitors, and treatment effects between Etanercept and TNFRI variants were compared. Cyclosporine A was used as a positive control group.

The dry eye syndrome animal model was constructed in reference to the existing known method (J Immunol 2011; 187; 3653-3662). Specifically, a parasympatholytic agent, Scopolamine (5 mg/ml), was subcutaneously administered to C57BL/6 mice 0.1 mL per each time, three times a day while using a controlled environmental chamber maintaining humidity of 40% or lower for 14 days, to thereby induce dry eye syndrome. After that, test materials were injected for 7 days and the degree of symptom improvement for each case was observed.

TNFRI variants and Etanercept were administered to mice with induced dry eye syndrome through eye drop application four times a day at a concentration of 2.5 mg/ml for 7 days. In addition, 0.05% of cyclosporine A was administered through eye drop administration two times a day for 7 days, and the degree of improvement in corneal damage was measured.

Corneal conditions were observed by the naked eye, and then the corneal damage was scored according to the severity of the symptom as shown in Table 3. Grade 0 means that no lesion was observed in the cornea; Grade 1 means that a leison was observed in about ⅓ the cornea; Grade 2 about ½; Grade 3 about ⅔; and Grade 4 almost the entire cornea.

As a result, it was confirmed that three of the TNFRI variants, HL036337, HL036326, and HL036330, were very effective in the degree of improvement in the corneal damage as compared with Etanercept, HL036402 (natural TNFRI), and cyclosporine A (see, FIG. 1)

TABLE 3

Corneal erosion grade

| Corneal Erosion Grade |
|---|
| Grade 0: no erosion |
| Grade 1: mild |
| Grade 2: mild to moderate |
| Grade 3: moderate |
| Grade 4: Severe |

Example 2

Verification of Treatment Effect of HL036337 Treatment in Dry Eye Syndrome Animal Model

Example 2.1

Verification of Corneal Damage Recovery Effect

HL036337, as a TNFRI variant, was prepared by using a buffer, to have concentrations of 0.625 mg/ml and 6.25 mg/ml, respectively, which was applied 8 L for each time, four times a day for eye drop, and applied 0.5 mg/kg and 5 mg/kg one time a day, respectively, for subcutaneous administration. In addition, Etanercept, as a control group, was subcutaneously applied 5 mg/kg one time a day.

Test materials were administered to the dry eye syndrome animal model constructed as described in Example 1 above, for 7 days, and then the degree of symptom improvement was observed. Etanercept was applied through subcutaneous administration, and TNFRI variants were applied through subcutaneous administration and eye drop administration.

The degree of corneal damage was evaluated in the same manner as Example 1 above.

As a result, while subcutaneous administration of Etanercept exhibited a little symptom improvement effect, subcutaneous administration and eye drop administration of TNFRI variants all exhibited corneal damage recovery effects, and particularly, eye drop administration exhibited remarkable effects of recovering corneal damage (see, FIG. 2).

In addition, it was confirmed that HL036326 and HL036330, as TNFRI variants, also exhibited corneal damage recovery effects in a similar degree to HL036337.

Example 2.2

Verification of Tear Volume Increase Effect

In order to verify the degree of tear volume increase due to administration of test materials, a Fluorescein paper was input on the lower eyelid and then the tear volume was measured. The grade according to the tear volume is as shown in Table 4. Grade 0 means that there was little tear in the paper; Grade 1 means that the paper was wet by 3 mm; Grade 2 by 2~4 mm; and Grade 3 by 6 mm.

TABLE 4

| Tear secretion grade | |
| --- | --- |
| Tear Secretion Grade | |
| Grade 0: no tear lake | |
| Grade 1: severe | 3 mm |
| Grade 2: moderate | 4~5 mm |
| Grade 3: mild | 6 mm |

Administration methods of the respective materials were the same as those in Example 2.1. As a result, it was confirmed that, in the case of equal dosage, HL036337, as TNFRI variant, exhibited a superior degree of tear volume recovery as compared with Etanercept, and eye drop administration groups of TNFRI variants had remarkable effects, such as recovering the tear volume to the almost normal level, similarly to the corneal damage recovery effect (see, FIG. 3).

It was confirmed that HL036326 and HL036330, as TNFRI variants, also exhibited the tear volume recovery effect in a similar degree to HL036337.

Example 2.3

Verification of Anti-Inflammatory Efficacy in Cornea

In order to verify of anti-inflammatory efficacy, mRNA was extracted from the corneal tissue and measurement of inflammation-related cytokine was carried out by using the qPCR method. Levels of mRNAs of IFN-γ, IL-1, IL-4, IL-6, IL-21, and IL-22 were confirmed.

Administration methods of the respective materials were the same as those in Example 2.1. As a result, it was confirmed that inflammation-related cytokines (IFN-γ, IL-1, IL-6, IL-4, IL-21, and IL-22) due to induction of dry eye syndrome were significantly increased. However, it was confirmed that subcutaneous administration of HL036337 as the TNFRI variant reduced inflammation-related cytokines, and particularly, eye drop administration thereof had remarkable effects, such as, improving the degree of inflammation to recovery of an almost normal level. Whereas, in the case of subcutaneous administration of Etanercept, the inflammation reduction effect was hardly observed (see, FIG. 4).

It was confirmed that HL036326 and HL036330, as TNFRI variants, also exhibited anti-inflammatory effects in the cornea in a similar degree to HL036337.

Example 2.4

Verification of Anti-Inflammatory Efficacy on Ocular Surface

In order to determine the amount of inflammatory cytokines on the ocular surface, measurement thereof was carried out by using the Luminex 100. The amounts of IFN-γ, IL-6, IL-21, and IL-22 were measured.

A solution containing 6.25 mg/ml of TNFRI variants HL036337 was prepared by using buffer, and the solution was administered to mice with induced dry eye syndrome through eye drop (four times a day, 8 μl at a time), and subcutaneously (once a day, 5 mg/kg dose). In addition, Etanercept was administered to mice with induced dry eye syndrome subcutaneously (once a day, 5 mg/kg dose).

The mice with induced dry eye were prepared as described in Example 1. HL036337 and Etanercept were administered for 7 days, and the anti-inflammatory efficacy on ocular surface was measured.

As a result, inflammation-related cytokines (IFN-γ, IL-6, IL-21, and IL-22) were remarkably increased on the ocular surface due to the induction of dry eye syndrome. In the case of eye drop administration of HL036337 as the TNFRI variant, a remarkable inflammation improvement effect was observed. However, in the case of subcutaneous administration of Etanercept, the inflammation reduction effect was hardly observed.

It was confirmed that HL036326 and HL036330, as TNFRI variants, also exhibited anti-inflammatory effects on the ocular surface in a similar degree to HL036337.

Example 2.5

Verification of Anti-Inflammatory Efficacy on Lacrimal Gland

In order to compare effects between 0.05% cyclosporine A, currently in use, as a therapeutic agent for dry eye syndrome, and 0.1% methyl prednisolone eye drop, the amounts of inflammatory cytokines in the lacrimal gland were measured, mRNA was extracted from the lacrimal gland tissue and measurement of inflammation-related cytokines was carried out by using the qPCR method. Levels of mRNAs of IFN-γ and IL-6 were confirmed.

A solution containing 6.25 mg/ml of TNFRI variants HL036337 was prepared by using buffer, and the solution was administered to mice with induced dry eye syndrome through eye drop (four times a day, 8 ?l at a time), and Etanercept was administered to mice with induced dry eye syndrome subcutaneously (once a day, 5 mg/kg dose).

The mice with induced dry eye were prepared as described in Example 1. HL036337 and Etanercept were administered for 7 days, and the anti-inflammatory efficacy on Lacrimal Gland was measured.

As a result, it was observed that the inflammation-related cytokines (IFN-γ and IL-6) due to the induction of dry eye syndrome are remarkably increased in the lacrimal gland, and eye drop application of HL036337 as the TNFRI variant had an equal effect as compared with eye drop application of methyl prednisolone. However, it was observed that cyclosporine A had a slight effect below that of HL036337 or methyl prednisolone (see, FIG. 6).

It was confirmed that HL036326 and HL036330, as TNFRI variants, also exhibited anti-inflammatory effects in the lacrimal gland in a similar degree to HL036337.

INDUSTRIAL APPLICABILITY

As described above, the modified TNFRI or modified TNFRI fragment of the present invention has excellent TNFα neutralizing activity, and inhibits TNFα activity on the ocular surface of the patient to suppress inflammation induction effects related to the dry eye syndrome. Therefore, the modified TNFRI or modified TNFRI fragment of the present invention exhibits remarkable effects in the prevention and treatment of dry eye syndrome, and thus can be very useful in the prevention and treatment of dry eye syndrome.

The present invention has been described in detail based on particular features thereof, and it is obvious to those skilled in the art that these specific technologies are merely preferable embodiments and thus the scope of the present invention is not limited to the embodiments. Therefore, the substantial scope of the present invention is defined by the accompanying claims and equivalent thereof.

The invention claimed is:

1. A method of treating dry eye syndrome comprising administering a composition comprising at least one modified tumor necrosis factor receptor-1 polypeptides (TNFRI) or modified TNFRI fragment,
wherein the modified TNFRI or the modified TNFRI fragment comprises amino acid sequence
iii) comprising the modifications of 5 amino acid residues at positions 68, 92, 95, 97 and 98 selected from the group consisting of L68V/S92I/H95F/R97P/H98A, L68V/S92M/H95F/R97P/H98A and L68V/S92M/H95F/R97P/H98G, and additional modification of an amino acid residue at position K161N or D207N in an amino acid sequence of a natural TNFRI as set forth in SEQ ID NO:1 or an amino acid sequence of a TNFRI fragment.

2. The method of treating dry eye syndrome according to claim 1,
wherein the modified TNFRI or the modified TNFRI fragment comprises amino acid sequences selected from the group:
i) an amino acid sequence including amino acid modification selected from L68V/S92I/H95F/R97P/H98A/K161N, L68V/S92M/H95F/R97P/H98A/D207N and L68V/S92M/H95F/R97P/H98G/K161N in the amino acid sequence of the natural TNFRI set forth in SEQ ID NO: 1 (TNFRI);
ii) an amino acid sequence including amino acid modification selected from L68V/S92I/H95F/R97P/H98A/K161N, L68V/S92M/H95F/R97P/H98A/D207N, and L68V/S92M/H95F/R97P/H98G/K161N in the amino acid sequence composed of amino acid residues 41 to 211 of the amino acid sequence of the natural TNFRI set forth in SEQ ID NO: 1 (TNFRI171); and
iii) an amino acid sequence including amino acid modification selected from L68V/S92I/H95F/R97P/H98A/K161N, and L68V/S92M/H95F/R97P/H98G/K161N in the amino acid sequence composed of amino acid residues 41 to 166 of the amino acid sequence of the natural TNFRI set forth in SEQ ID NO: 1 (TNFRI126).

3. The method of treating dry eye syndrome according to claim 2,
wherein the modified TNFRI or the modified TNFRI fragment comprises amino acid sequences selected from the group:
i) an amino acid sequence including amino acid modification selected from L68V/S92M/H95F/R97P/H98G/K161N and L68V/S92M/H95F/R97P/H98A/D207N in the amino acid sequence of the natural TNFRI set forth in SEQ ID NO: 1 (TNFRI); and
ii) an amino acid sequence including amino acid modification selected from L68V/S92M/H95F/R97P/H98G/K161N and L68V/S92M/H95F/R97P/H98A/D207 in the amino acid sequence composed of amino acid residues 41 to 211 of the amino acid sequence of the natural TNFRI set forth in SEQ ID NO: 1 (TNFRI171).

4. The method of treating dry eye syndrome according to claim 2,
wherein the modified TNFRI or the modified TNFRI fragment comprises amino acid sequence of SEQ ID NOs: 18 or 20.

5. The method of treating dry eye syndrome according to claim 2,
wherein the modified TNFRI or the modified TNFRI fragment further comprises modification for production of the modified TNFRI or the modified TNFRI fragment in E. coli.

6. The method of treating dry eye syndrome according to claim 5,
wherein the modification for production of the modified TNFRI or the modified TNFRI fragment in E. coli is addition of a signal sequence or methionine to the amino terminus of the modified TNFRI or the modified TNFRI fragment.

7. The method of treating dry eye syndrome according to claim 1, wherein the composition comprising at least one polypeptide complex which at least two modified TNFRI or modified TNFRI fragment are linked by covalent bond.

8. The method of treating dry eye syndrome according to claim 1,
wherein the modified TNFRI or modified TNFRI fragment further comprises modification(s),
wherein the modification(s) is(are) glycosylation, acylation, methylation, phosphorylation, hasylation, carbamylation, sulfation, prenylation, oxidation, guanidination, amidination, carbamylation, trinitrophenylation, nitration, or PEGylation.

9. A method of treating dry eye syndrome comprising administering a topical drug formulation, wherein the formulation comprises at least one modified tumor necrosis factor receptor-1 polypeptides (TNFRI) or modified TNFRI fragment,
> wherein the modified TNFRI or the modified TNFRI fragment comprises amino acid sequences comprising modifications of 5 amino acid residues at positions 68, 92, 95, 97 and 98 selected from the group consisting of L68V/S92I/H95F/R97P/H98A, L68V/S92M/H95F/R97P/H98A and L68V/S92M/H95F/R97P/H98G, and additional modification of an amino acid residue at position K161N or D207N in an amino acid sequence of a natural TNFRI as set forth in SEQ ID NO:1 or an amino acid sequence of a TNFRI fragment.

10. The method of treating dry eye syndrome according to claim 9, wherein the topical drug formulation comprises an eye drop or eye ointment formulation.

11. A method of treating dry eye syndrome comprising administering a composition comprising at least one modified tumor necrosis factor receptor-1 polypeptides (TNFRI) or modified TNFRI fragment, wherein the modified TNFRI or the modified TNFRI fragment comprises amino acid sequence including amino acid modification L68V/S92M/H95F/R97P/H98G/K161N in the amino acid sequence composed of amino acid residues 41 to 211 of the amino acid sequence of the natural TNFRI set forth in SEQ ID NO: 1 (TNFRI171).

12. A method of treating keratoconjunctivitis sicca comprising administering a composition comprising at least one modified tumor necrosis factor receptor-1 polypeptides (TNFRI) or modified TNFRI fragment,
> wherein the modified TNFRI or the modified TNFRI fragment comprises amino acid sequence including the modifications of 5 amino acid residues at positions 68, 92, 95, 97 and 98 selected from the group consisting of L68V/S92I/H95F/R97P/H98A, L68V/S92M/H95F/R97P/H98A and L68V/S92M/H95F/R97P/H98G, and additional modification of an amino acid residue at position K161N or D207N in an amino acid sequence of a natural TNFRI as set forth in SEQ ID NO:1 or an amino acid sequence of a TNFRI fragment.

13. A method of treating keratoconjunctivitis sicca comprising administering a composition comprising at least one modified tumor necrosis factor receptor-1 polypeptides (TNFRI) or modified TNFRI fragment, wherein the modified TNFRI or the modified TNFRI fragment comprises amino acid sequence including amino acid modification L68V/S92M/H95F/R97P/H98G/K161N in the amino acid sequence composed of amino acid residues 41 to 211 of the amino acid sequence of the natural TNFRI set forth in SEQ ID NO: 1 (TNFRI171).

* * * * *

UNITED STATES PATENT AND TRADEMARK OFFICE
CERTIFICATE OF CORRECTION

| | | |
|---|---|---|
| PATENT NO. | : 9,580,490 B2 | Page 1 of 1 |
| APPLICATION NO. | : 14/404001 | |
| DATED | : February 28, 2017 | |
| INVENTOR(S) | : Sung Wuk Kim et al. | |

It is certified that error appears in the above-identified patent and that said Letters Patent is hereby corrected as shown below:

In the Specification

Column 5, Lines 20-21: "and sub-situation of H" should be --and substitution of H--.

Column 12, Line 59: "and pETTNFRI171_A30" should be --and pET-TNFRI171_A30--.

Column 19, Line 10: "8 ?l at a time" should be --8 µl at a time--.

In the Claims

Column 61, Lines 27-28: "sequence iii) comprising the" should be --sequence comprising the--.

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*